(12) United States Patent
Kapec et al.

(10) Patent No.: US 9,877,761 B2
(45) Date of Patent: Jan. 30, 2018

(54) APPLICATOR WITH CONFORMABLE TIP

(75) Inventors: Jeffrey Kapec, Irvington, NY (US);
Kazuna Tanaka, Irvington, NY (US);
Yukiko Naoi, Irvington, NY (US);
Marci Wirtz, Irvington, NY (US)

(73) Assignee: Abyrx Inc., Irvington, NY (US)

( * ) Notice: Subject to any disclaimer, the term of this patent is extended or adjusted under 35 U.S.C. 154(b) by 867 days.

(21) Appl. No.: 14/124,122

(22) PCT Filed: Jun. 7, 2012

(86) PCT No.: PCT/US2012/041372
§ 371 (c)(1),
(2), (4) Date: Dec. 4, 2014

(87) PCT Pub. No.: WO2012/170700
PCT Pub. Date: Dec. 13, 2012

(65) Prior Publication Data
US 2015/0105785 A1   Apr. 16, 2015

Related U.S. Application Data

(60) Provisional application No. 61/494,335, filed on Jun. 7, 2011.

(51) Int. Cl.
*A61B 17/88* (2006.01)
*A61M 37/00* (2006.01)
(52) U.S. Cl.
CPC ...... *A61B 17/8811* (2013.01); *A61B 17/8825* (2013.01); *A61B 17/8836* (2013.01); *A61M 37/00* (2013.01)

(58) Field of Classification Search
CPC .. A61B 17/88; A61B 17/8811; A61B 17/8836
See application file for complete search history.

(56) References Cited

U.S. PATENT DOCUMENTS

| 5,685,879 | A | * | 11/1997 | Phillips | ................. | A61B 17/88 424/426 |
| 6,019,765 | A | * | 2/2000 | Thornhill | .............. | A61F 2/4601 606/93 |
| 6,331,312 | B1 | | 12/2001 | Lee et al. | | |
| 6,692,469 | B1 | | 2/2004 | Weekes et al. | | |
| 7,329,241 | B2 | | 2/2008 | Horvath et al. | | |
| 8,002,843 | B2 | | 8/2011 | Knaack et al. | | |

(Continued)

OTHER PUBLICATIONS

International Search Report issued for PCT/US2012/041372 dated Jan. 29, 2013.

*Primary Examiner* — Christopher Beccia
(74) *Attorney, Agent, or Firm* — Mintz Levin Cohn Ferris Glovsky and Popeo, P.C.; Muriel Liberto, Esq.

(57) ABSTRACT

Described herein are applicators for delivery of a viscous material to a bone surface and methods of use. The applicator includes an elongate handle portion and a tip coupled to a distal location of the handle portion and formed of an elastomeric material configured to conform to the bone surface. The tip includes a bend a distance away from the distal location, a contact surface distal to the bend and including one or more surface features configured to adhere to the viscous material, and a front end having a conic curvature. The bend is between about 20 degrees to about 40 degrees from a longitudinal axis of the tip.

28 Claims, 8 Drawing Sheets

(56) References Cited

U.S. PATENT DOCUMENTS

| | | | |
|---|---|---|---|
| 2004/0092946 A1* | 5/2004 | Bagga | A61B 17/16 606/93 |
| 2005/0065214 A1 | 3/2005 | Kronenthal | |
| 2005/0216018 A1* | 9/2005 | Sennett | A61B 17/1604 606/79 |
| 2006/0002976 A1 | 1/2006 | Kronenthal | |
| 2006/0216323 A1 | 9/2006 | Knaack et al. | |
| 2006/0280801 A1 | 12/2006 | Kronenthal | |
| 2007/0299426 A1* | 12/2007 | Trieu | A61B 17/8836 604/890.1 |
| 2009/0082719 A1 | 3/2009 | Yeung | |
| 2009/0157085 A1 | 6/2009 | Melsheimer | |
| 2010/0168638 A1* | 7/2010 | Korogi | A61M 35/006 604/3 |
| 2010/0179507 A1 | 7/2010 | Hess et al. | |
| 2011/0062189 A1 | 3/2011 | Kapec et al. | |
| 2011/0313396 A1* | 12/2011 | Chanoch | A61M 5/31561 604/506 |

* cited by examiner

APPLICATOR WITH CONFORMABLE TIP

CROSS-REFERENCE TO RELATED APPLICATIONS

This application is a 35 U.S.C. §371 national stage entry of PCT/US2012/041372, which has an international filing date of Jun. 7, 2012 and claims priority to U.S. Provisional Patent Application No. 61/494,335, filed on Jun. 7, 2011, the disclosures of which are incorporated herein by reference in their entireties.

BACKGROUND

Bone waxes (and other semi-rigid surgery-related biomaterials) are often pressed onto the blade of a spatula-like surgical instrument (e.g. Penfield dissector) and subsequently pressed into a bleeding bone defect to staunch bleeding. Application of bone wax in this way relies on frictional adherence, both to secure the wax to the bone as well as for its release and removal from the surgical instrument. This mode of application is often inadequate for softer or more flowable, and/or putty like biomaterials.

SUMMARY

The subject matter described herein is related to devices and systems that can be used to deliver and manipulate implantable putty-like biomaterials in bone that are soft and flowable.

In one aspect, disclosed herein is an applicator for delivery of a viscous material to a bone surface including an elongate handle portion; and a tip coupled to a distal location of the handle portion and formed of an elastomeric material configured to conform to the bone surface. The tip includes a bend a distance away from the distal location. The bend is between about 20 degrees to about 40 degrees from a longitudinal axis of the tip. The tip also includes a contact surface distal to the bend and including one or more surface features configured to adhere to the viscous material. The tip also includes a front end having a conic curvature.

In another aspect, disclosed herein is a method for filing a hole in a bone surface including maintaining an amount of a viscous material on an applicator tip having an elastomeric material configured to conform to the bone surface; a contact surface located distal to a bend and having one or more surface features configured to adhere to the viscous material; and edges having a conic curvature. The method also includes applying the viscous material intraoperatively to the hole in the bone surface using the contact surface of the applicator tip.

More details of the devices, systems and methods are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings. Generally speaking the figures are not to scale in absolute terms or comparatively but are intended to be illustrative of claimed features. Also, relative placement of features and elements may be modified for the purpose of illustrative clarity.

DETAILED DESCRIPTION

Described herein are devices, systems and methods for intraoperative delivery and application of implantable compositions into irregular biological tissue surfaces such as an osseous defect in the presence of surgery associated fluids such as blood and irrigants. The devices, systems and methods disclosed are useful for the control of osseous hemorrhage due to surgical intervention or trauma, implantation of drug delivering putties and/or for providing structural putties such as osteoconductive matrices, tissue bulking agents or hardening surgical cements to the body.

The devices described herein feature, flexible conformal tips configured to facilitate the application of viscous biomaterials such as putties, hydrogels and cements (setting and non-setting). The conformal nature of the tips can allow for the application of biomaterial in confined spaces, and for effective spreading of the biomaterial onto rough or irregular surfaces such as broken or cut bone. The conformal tips can also include an angular component, such as a beveled edge or angular blade. The angular component in combination with tip flexibility can allow for uniform application and spreading of the biomaterial on rough surfaces even in confined spaces when the approach is perpendicular or near perpendicular to the tissue surface needing treatment. The conformal tip may be in a generally solid form present on a static delivery device such as a spatula, or it may be hollow and serve as a component of a syringe or syringe-like delivery system.

The compositions that can be delivered using the devices described herein can vary and can include high viscosity biomaterials. The compositions generally can have high viscosity and the consistency of putty or putty-like compositions such as dough, modeling clay, glazier's putty and the like. The compositions can be generally soft, moldable, non-elastic, cohesive mixtures. Specific compositions include, for example, soft and hard tissue hemostats and tamponades, bone substitutes, bone void fillers, bone cements, tissue glues and bonding agents, and/or bulking agents and carriers for the delivery of therapeutic agents. The compositions can include those described in U.S. Patent Application Serial Nos. 2006-0002976, filed Sep. 16, 2004; 2006-0280801, filed Jul. 25, 2006; and 2005-0065214, filed Sep. 16, 2004 each by Kronenthal, and which are each incorporated herein by reference in their entireties. In some embodiments, the compositions are settable biomaterials, including settable ceramics (see, for example, Lee et al. U.S. Pat. No. 6,331,312, which is incorporated herein by reference) or polymers (see, for example, Knaack US 2006-0216323, and Knaack, et al. U.S. Pat. No. 8,002,843, which are also incorporated herein by reference). Many of the compositions can also include bioactive substituents such as growth factors, clotting agents or therapeutic drugs. The compositions can also include osteoconductive or osteoinductive particles such as materials ranging in size from about 25 to about 5000 microns in dimension. In cases where the composition to be applied is not appropriately soft or spreadable at room temperature, a heating element may be provided on the device (e.g. a heating coil) to soften or melt the product to aid in delivery.

The conformal tips are affixed to the delivery device with a specified angle (ie, the angle of a blade or the bevel of a hollow tip) on the distal application surface which aids in the precise application and spreading of the material to be applied onto a surgical site such as cut bone or soft tissue.

Figure 1:
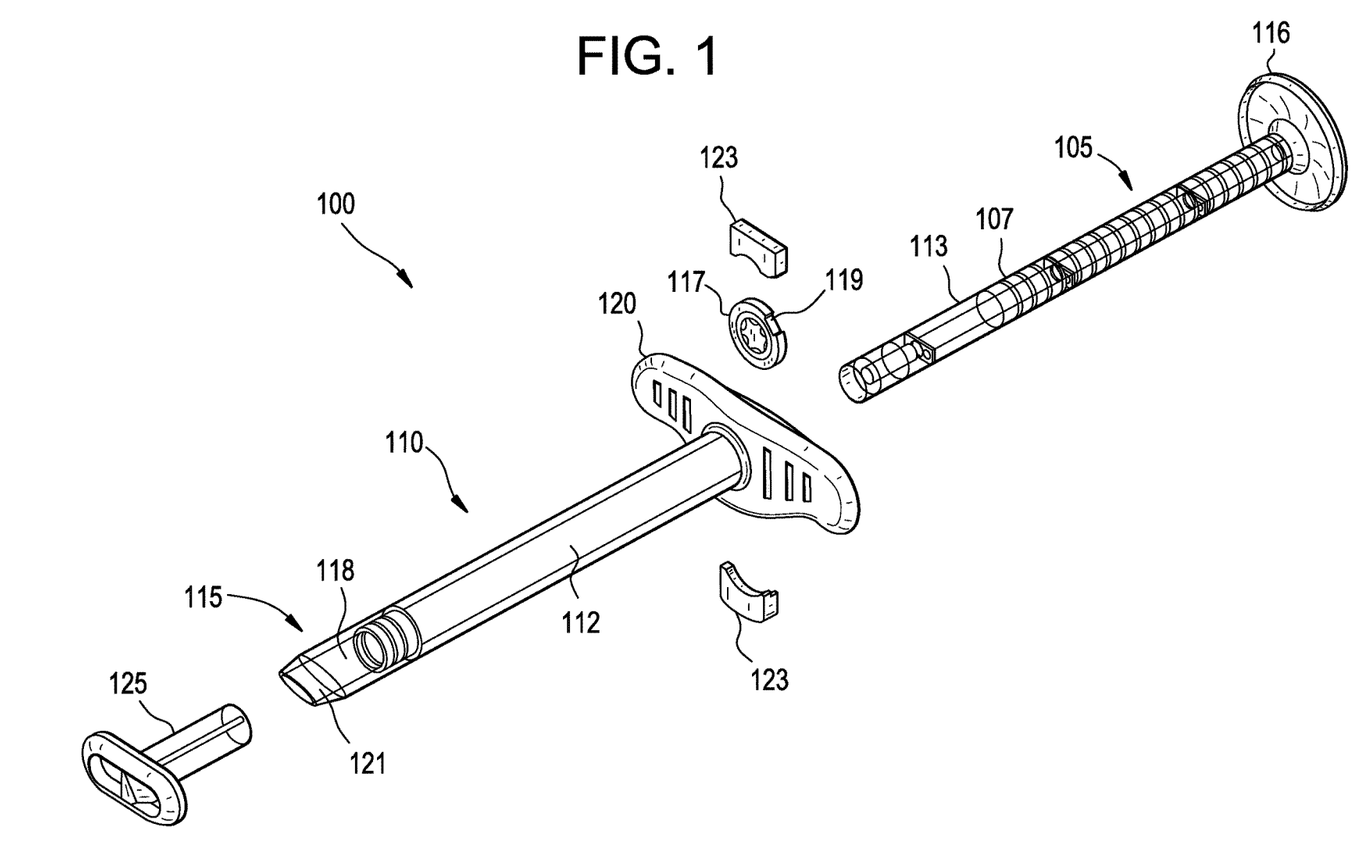
FIG. 1 depicts an exploded, perspective view of an embodiment of an applicator as described herein.

FIG. 1 is an exploded view of an embodiment of an applicator 100. The applicator 100 can include a plunger 105, a barrel 110, and a tip 115. The barrel 110 can be an elongate element having a central bore 112 running therethrough that can house an amount of a material for delivery. The tip 115 is a generally short component reversibly coupled to a distal end region of the barrel 110. The tip 115 can be formed of a flexible material as will be described in more detail below and can be configured to effectively apply and/or wipe the composition to be delivered onto a tissue surface, such as a boney surface. The plunger 105 can include a distal elongate portion 113 coupled to a proximal flange 116. The distal elongate portion 113 of the plunger 105 can have an outer diameter that is slightly less than the diameter of the bore 112 such that the plunger 105 can be inserted through the bore 112 of the barrel 110 and travel a distance within the bore 112 for extrusion of the material housed within the bore 112. Similarly, the plunger 105 has a cross-sectional shape that matches the cross-sectional shape of the barrel 110. The barrel 110 and plunger 105 can be generally cylindrical in shape although other cross-sectional shapes are considered herein. Optionally, a cylindrical tip (not shown) can be present on the plunger 105 that can contact the inner barrel wall to provide a seal against backflow of the composition to be delivered. The tip can be formed of a flexible biomaterial such as a biocompatible rubber or elastomer.

It should be appreciated that the applicator 100 need not include a barrel 110 and plunger 105. For example, in some embodiments, the applicator 100 can include a spatula having a handle and a flexible tip with an angled flat application surface at a distal end of the handle. The application surface can be configured to conform to a rough surface to allow for the uniform spreading of the composition. In one embodiment, either or both surfaces of the flexible tip are smooth. An upper or lower surface of the flexible tip can also have one or more features that are fabricated from a material to which the composition can, to some degree, adhere. In some embodiments, the feature may include projecting or recessed surface texturing such as dimples, ridges, bristles, hairs. The feature can be rigid or flexible. The feature can allow for pre-loading of the spatula with an amount of the composition to be presented to the surgical site where the composition can then be applied, such as using a wiping motion. It should be appreciated that the flexible tip can be removable or fixed to the applicator 100. In some embodiments, the handle end of the applicator 100 can have a surface feature such as one or more barbs the hold the flexible tip in place once slipped onto a distal end of the applicator 100.

Again with FIG. 1, the tip 115 can be a generally short component coupled to the distal end region of the barrel 110. A proximal end of the tip 115 can mechanically interface with a distal end of the barrel 110 such that the tip 115 can be optionally removable. In an embodiment, the tip 115 and barrel 110 interface via a lap joint and retention groove, and are permanently bonded. In another embodiment, a short pin or other structural shape is molded onto the outer surface of the barrel to mate with a complementary hole on the tip to further secure the tip to the barrel. The interface between the tip 115 and the barrel 110 can transition such that the outer surfaces of the tip 115 and barrel 110 are flush and the inner surfaces are smooth. Removable or interchangeable tips can be advantageous such as when the applicator is provided as part of a kit. A surgeon can select tips of particular sizes or bevel angles depending on the features of the application site.

The tip 115 can have a central lumen 118 through which material extruded from the bore 112 of the barrel 110 can be delivered to a treatment site. The dimensions of the tip 115 can vary. The inner diameter of the tip 115 can be at least about 0.1 cm, 0.50 cm, 0.55 cm, 0.60 cm, 0.65 cm, 0.70 cm, 0.75 cm, 0.80 cm, 0.85 cm, or larger. In an embodiment, the inner diameter of the tip 115 is approximately 0.67 cm. The cross-section of the central lumen 118 can be generally circular to a generally oblong or oval cross-section. It is considered herein that the lumen 118 can be of virtually any cross-sectional shape such as round, angular or a combination, ranging from round to oval, to triangular, square, or polygonal. It should be appreciated that the barrel 110, the plunger 105 and the click washer 117 can each have alternative geometries to accommodate the cross section profile. The applicator 100 can also include a removable tip plug 125 that can be inserted through at least a portion of the central lumen 118 when the applicator 100 is not in use to prevent inadvertent extrusion of material from within the bore 112. Alternative embodiments of the tip plug include a cap which is secured around the outside of the tip.

Figure 2:
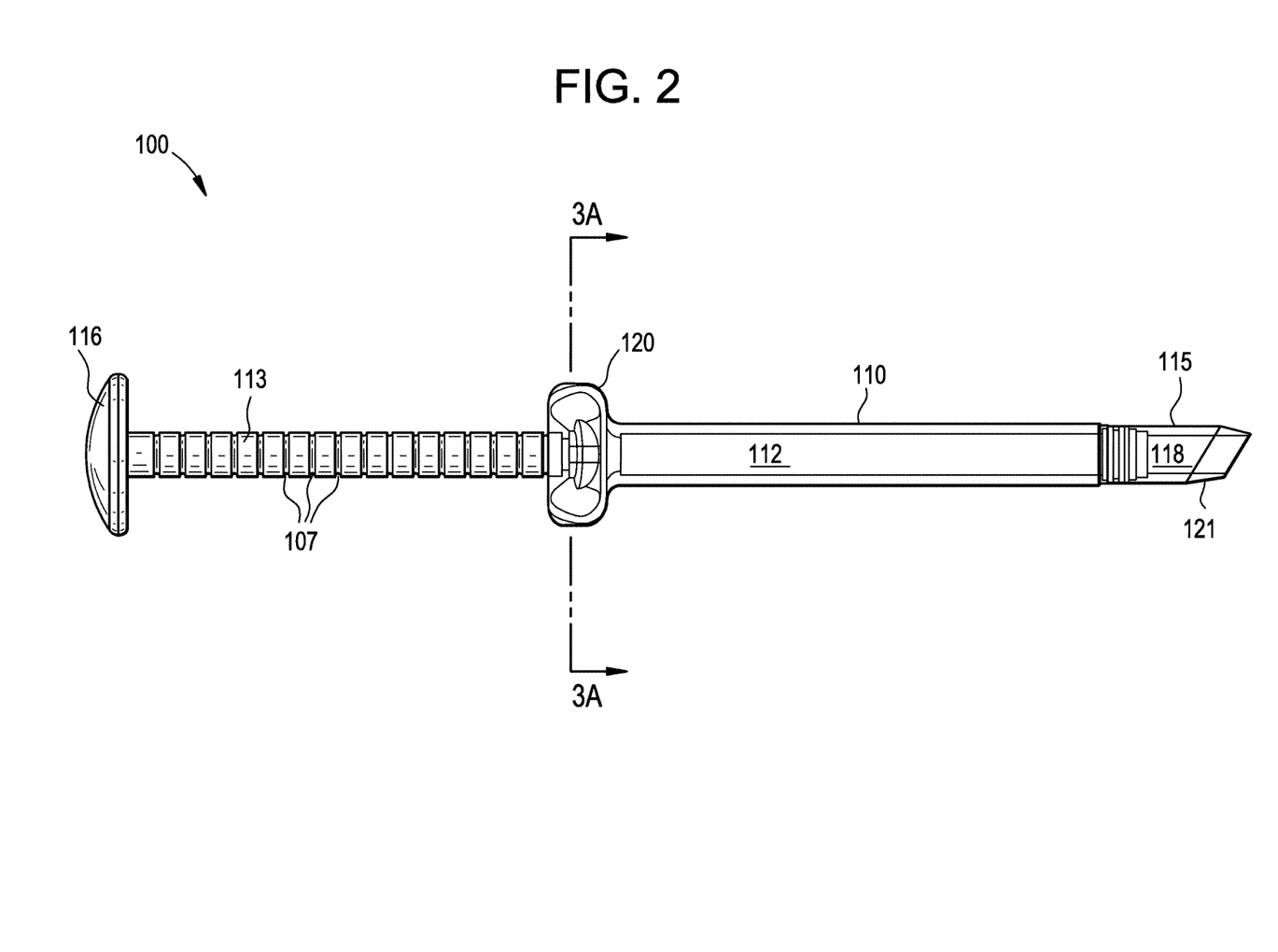
FIG. 2 depicts a side view of the assembled applicator of FIG. 1.

As best shown in FIG. 2, the tip 115 can include a bevel 121 a distance away from where the tip 115 couples to the barrel 110. The angle of the bevel 121 can vary. In an embodiment, the bevel 121 can be about 0 degrees such that the tip is perpendicular to the longitudinal axis to between about 20 degrees to about 50 or 60 degrees from the longitudinal axis of the tip 115. In another embodiment, the bevel 121 is approximately 30 degrees from the longitudinal axis of the tip 115. The angle of the bevel 121 can be optimized depending on the specific surgical application. The angle of the bevel can vary depending upon the need for flexibility in approach angle to the surgical site and the extent to which the composition will be wiped or spread onto the surgical site. In some embodiments, the bevel angle can be approximately 45 degrees to facilitate application of the composition from an approach angle of approximately 90 degrees. In some embodiments, shallower bevel angles of approximately 30 degrees are used where a greater variety of approach angles are anticipated. In one embodiment, one edge of the tip extends outward from one side of the tip lumen to a distance of from several millimeters to a centimeter or more to form a blade, such that the composition can first be extruded onto the blade, and subsequently applied to the surgical site with the aid of the blade.

The tip 115 can be formed of an elastomeric material configured to conform to a bone surface. The tip 115 can be formed of a generally flexible material including, but not limited to medical rubbers and polyurethanes, and thermoplastic elastomer (TPE) compounds such as VERSAFLEX CL e85, VERSAFLEX M 3060, MEDALIST MD320, PELLATHANE, Polyurethanes, Silicone rubbers, and other similar TPEs. It should be appreciated that non-TPE flexible materials such as thin wall polyethylene and polypropylene can be used to form the tip 115 as well. The material selected for the tip 115 generally has a hardness of Shore A 30-110, preferably 50-85. The Shore A of the tip 115 can be selected to match the application requirements of the composition to be applied. The long edge of the bevel can serve as a vehicle to facilitate wiping of the composition into place. Tip material with greater Shore A value can be used to facilitate wiping of stiffer compositions. Likewise, shorter tips may benefit from lower shore A values (30-70), while tips of ¾ of an inch or more may benefit from higher shore A values (50-110) The barrel 110 and plunger 105 can be formed of a variety of materials, but generally are formed of a rigid polymer such as a copolyester, (e.g. glycol-modified polyethylene terephthalates such as Eastman Eastar mn 210 or mn 211), acrylics, polycarbonates, polyethylenes, polyurethanes, polypropylenes and other relatively clear or translucent amorphous plastics (eg Easman Durastar or Tritan and equivalents). The click washer can be formed generally from a durable elastomeric material having a Shore A value from about 60 to about 100. Suitable materials can include Nylon, HYTREL and CRASTIN or blends thereof (Dupont Corp.). Alternative embodiments employ metal or ceramic click washers.

The applicator 100 can also include molded finger grips 120 positioned near an upper or proximal region of the barrel 110. The finger grips 120 can be positioned a distance from the top of the plunger 105 such that a user can hold and apply pressure between the flange 116 of the plunger 105 and the finger grips 120 of the barrel 110 to dispense material from the applicator 100. The finger grips 120 can have a coating such as an elastomeric coating for ease of use. In an embodiment, the position of the finger grip 120 near the top of the barrel 110 can be adjustable by a user to change the distance from the top of the plunger 105.

The dimensions of each of the components can vary. For example, the inner diameter of the barrel 110 can be at least about 0.25 cm, 0.50 cm, 0.55 cm, 0.60 cm, 0.65 cm, 0.70 cm, 0.75 cm, 0.80 cm, 0.85 cm, or larger. In an embodiment, the inner diameter of the barrel 110 is approximately 0.77 cm. The length of the barrel 110 can vary as well. The barrel 110 can have a length that is at least about 2.5 cm, 3.0 cm, 3.5 cm, 4.0 cm, 4.5 cm, 5.0 cm, 5.5 cm, 6.0 cm, 6.5 cm, 7.0 cm, 7.5 cm, 8.0 cm or greater. In an embodiment, the barrel 110 has a length of about 7.2 cm. The fluid capacity (i.e. sample holding volume) of the barrel 110 can vary as well. The barrel 110 can have a fluid capacity that is at least about 1.0 cc, 1.5 cc, 2.0 cc, 2.5 cc, 3.0 cc, 3.1 cc, 3.2 cc, 3.3 cc, 3.4 cc, 3.5 cc, or greater. In an embodiment, the barrel 110 is approximately 7.2 cm in length and has a fluid capacity of approximately 3.35 cc. In some embodiments, it may be necessary to use a barrel length significantly exceeding 10 cm. For example, in minimally invasive surgical applications it may be anticipated that the composition within the device will fill only a small portion of the barrel volume (e.g. <7 cm length) and a correspondingly long plunger may be used.

As mentioned above, the plunger 105 can optionally deliver precisely controlled aliquots of material from the barrel 110. Any number of mechanisms known to the art may be employed for dose control, including the use of a threaded plunger, ratchet control mechanisms, as well as other means (see, for example, Horvath et al, U.S. Pat. No. 7,329,241, which is incorporated herein by reference) In some embodiments, the plunger 105 includes a series of grooves 107 on at least a portion of the outer surface of the distal elongate portion 113 (see again FIG. 2). The grooves 107 interface with a dispense mechanism. The dispense mechanism can include a click washer 117 coupled to the barrel 110 by one or more washer plugs 123. The click washer 117 can be positioned at or near the opening of the central bore 112. The click washer 117 can include a central aperture 119 aligned to surround the opening to the central bore 112 such that the elongate portion 113 of the plunger 105 inserts through the aperture 119 when inserted to the central bore 112.

Figure 3A:
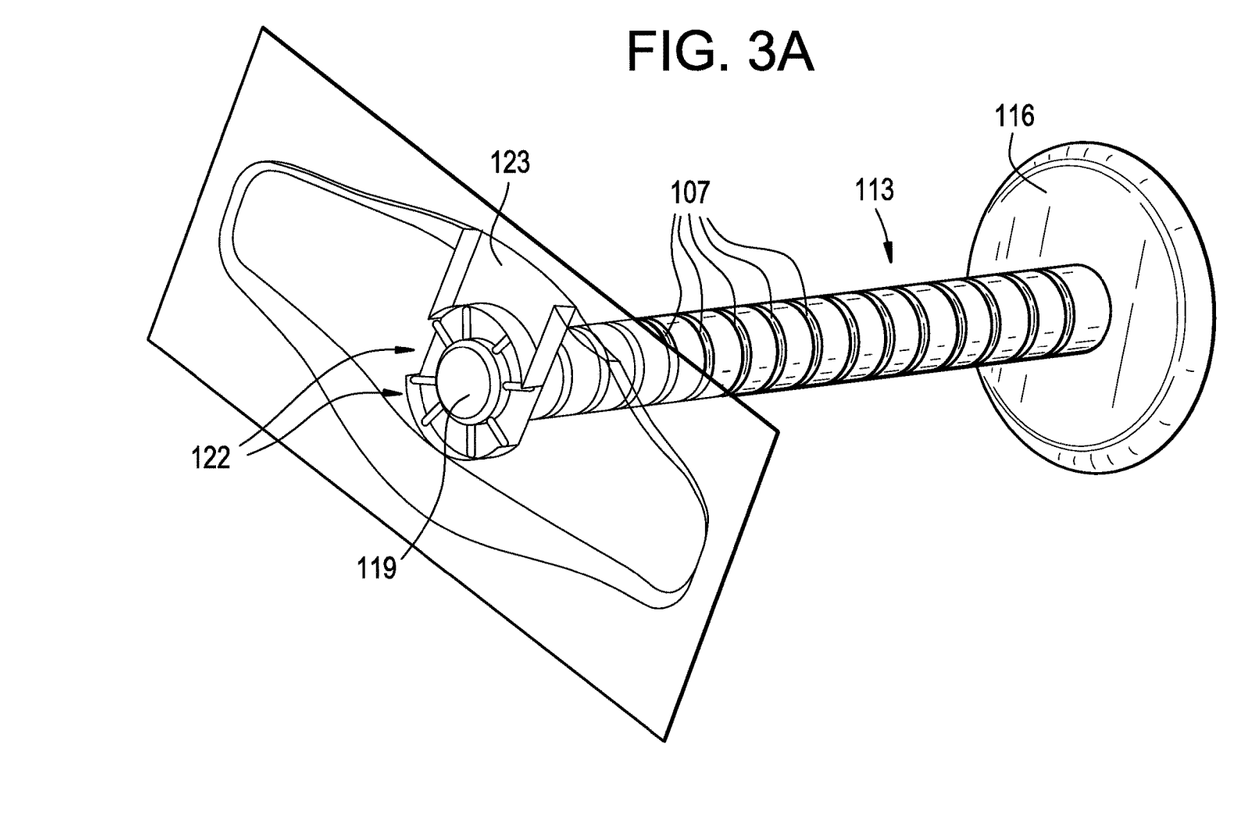
FIG. 3A depicts a cross-sectional view of the applicator from FIG. 2 taken along line 3A-3A.
Figure 3B:
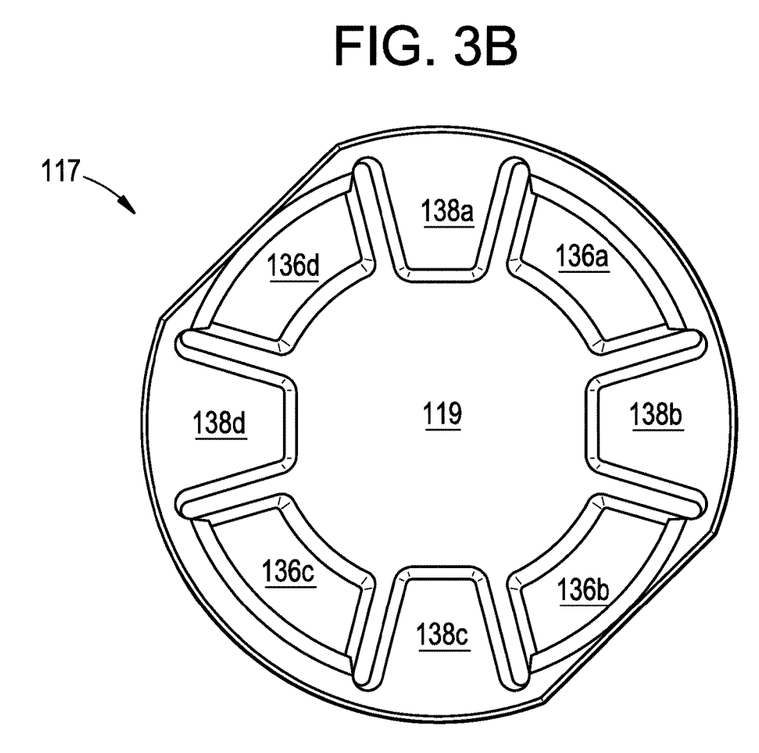
FIG. 3B depicts a top view of an embodiment of a click washer.

As best shown in FIGS. 3A and 3B, the click washer 117 can be formed by a series of teeth 122 connected at an outer perimeter and extending towards the central aperture 119. A first set of the teeth 136a, 136b, 136c, 136d can have a first length and alternate with a second set of teeth 138a, 138b, 138c, 138d that can have a second, longer length. The second set of teeth 138a, 138b, 138c, 138d can undergo limited relative movement to the first set of the teeth 136a, 136b, 136c, 136d providing for the diameter of the central aperture 119 to change depending on the position of the second set of teeth 138a, 138b, 138c, 138d. This allows for the click washer 117 to accommodate the variations in outer diameter of the elongate portion 113 of the plunger 105 caused by the series of grooves 107.

The second set of teeth 138a, 138b, 138c, 138d reversibly interface with the grooves 107 as the plunger 105 is urged through the central aperture 119 of the click washer 117. For example, the second set of teeth 138a, 138b, 138c, 138d can interface with a first groove 107 having a first, smaller diameter. Application of a force against the flange 116 of the plunger 105 can urge the plunger 105 past the click washer 117 such that the second set of teeth 138a, 138b, 138c, 138d move a degree relative to the first set of the teeth 136a, 136b, 136c, 136d and the central aperture 119 can accept a region of the plunger 105 adjacent the first groove 107 that has a second, larger diameter. As the plunger 105 is urged further into the barrel 110 a second groove 107 approaches the click washer 117 until the second set of teeth 138a, 138b, 138c, 138d snap into the second groove 107 and provide resistance to further advancement of the plunger 105 into the barrel 110. A user can again apply a force against the flange 116 of the plunger 105 causing the second set of teeth 138a, 138b, 138c, 138d of the click washer 117 to give way and once again allow the plunger 105 to travel in a distal direction further into the bore 112 of the barrel 110. Thus, the washer 117 accommodates both the larger diameter regions of the elongate portion 113 adjacent to the smaller diameter grooves 107 and the smaller diameter grooves 107.

The number of grooves 107 and click positions of the plunger 105 can vary as can the number of aliquots dispensed from the barrel 110. The plunger 105 can include 2, 3, 4, 5, 6, 7, 8, 10 or more grooves 107. In an embodiment, the plunger 105 includes at least 2 click positions such that at least one aliquot of material can be extruded from the barrel 110. In another embodiment, the plunger 105 includes at least 3 click positions such that at least two aliquots of material can be extruded from the barrel 110. In another embodiment, a single aliquot of material to be delivered is formed by more than a single click position. A single aliquot of material to be delivered can be formed by 2, 3, 4, 5, 6, 7, 8, 9, 10 or more click positions. In another embodiment, the barrel has a larger volume of material than the number of click positions of the plunger 105 such that no aliquot dispensed is less than the desired amount to be delivered. As an example, the barrel 110 can be configured to hold 3 aliquots of material and the plunger 105 can be configured to dispense only 2 aliquots of material from the barrel 110 such that a single aliquot remains within the barrel 110 as "slop." The click length can be the distance between a first outer groove 107 and a second outer groove 107 to dispense an amount of material within the barrel 110 through the tip 115. The click length can vary. In an embodiment, the click length can be at least about 0.20 cm, 0.25 cm, 0.30 cm, 0.35 cm, 0.40 cm, 0.45 cm, 0.50 cm or greater. In an embodiment, the click length can be at least about 0.35 cm. The volume of material dispensed from the barrel 110 with each click of the plunger 105 can vary and can be dependent upon the click length and the inner diameter of the barrel 110. The volume of material dispensed per click can be at least about 0.05 cc, 0.10 cc, 0.15 cc, 0.18 cc, 0.20 cc, 0.25 cc, 0.30 cc or greater. In an embodiment, the volume of material dispensed per click is 0.16 cc. This volume of material dispensed can correspond to a length of putty extruded. The length of putty extruded with each click can vary and can be at least about 0.20 cm, 0.25 cm, 0.30 cm, 0.35 cm, 0.40 cm, 0.45 cm, 0.50 cm, 0.55 cm, 0.60 cm or greater. In an embodiment, the length of putty extruded per click is 0.46 cm.

It should be appreciated that the applicators described herein can dispense any volume of material in a controlled manner and that volumes can vary. The volume of material delivered can be selected based on what is appropriate for the treatment for which the material is being used. Those skilled in the art will be aware of the amount of which the compositions are applied. The amounts will generally vary depending upon the application and the particular needs of the patient during surgery. In addition to the means described herein, the invention further encompasses the use of mechanically leveraged, hydraulic and or motorized applicators (see, for example, Weekes, et al. U.S. Pat. No. 6,692,469, the content of which is incorporated herein by reference).

Figure 4:
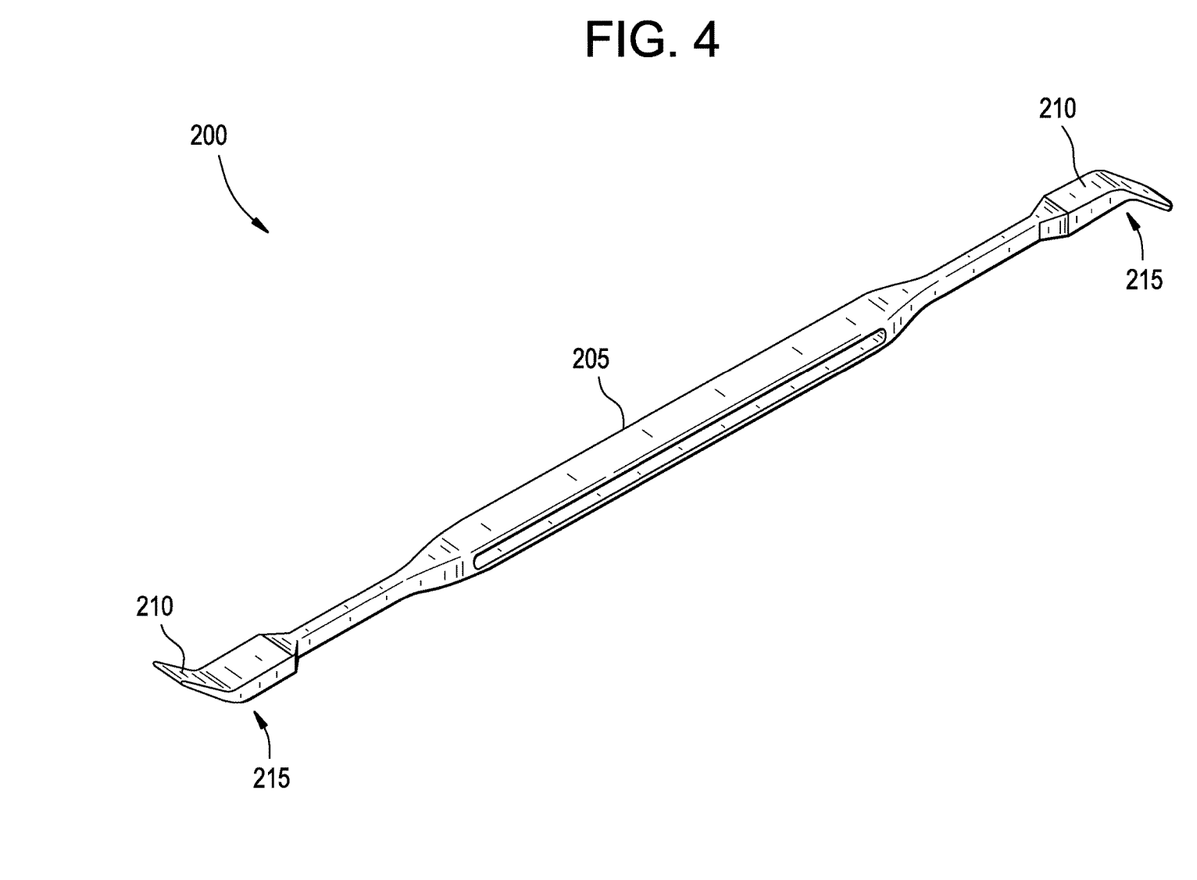
FIG. 4 depicts a perspective view of another embodiment of an applicator as described herein.
Figure 5A:
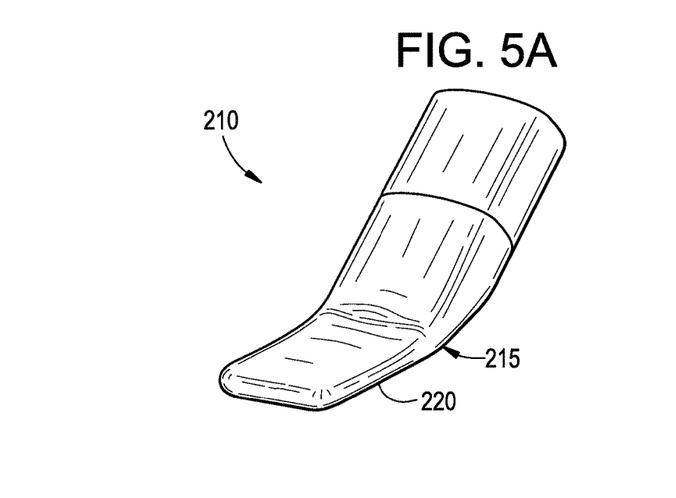
FIGS. 5A-5D depict perspective, top, side and cross-sectional views, respectively, of an embodiment of a tip of the applicator of FIG. 4.
Figure 5B:
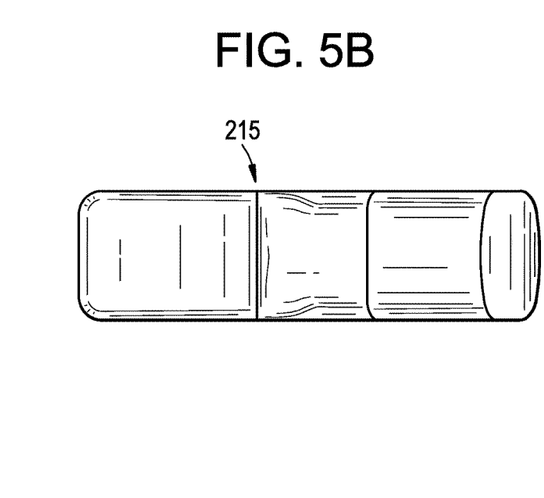
Figure 5C:
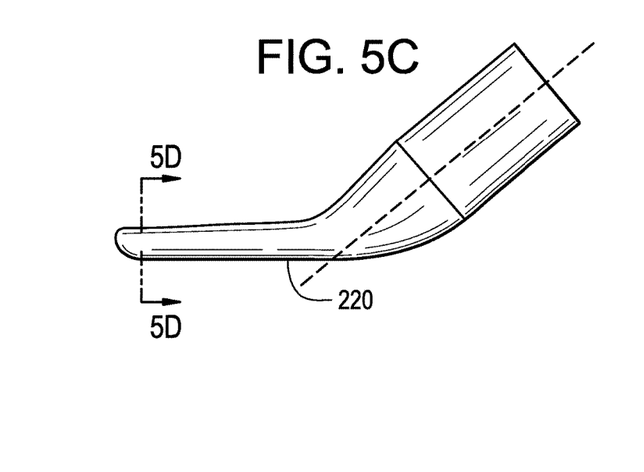
Figure 5D:
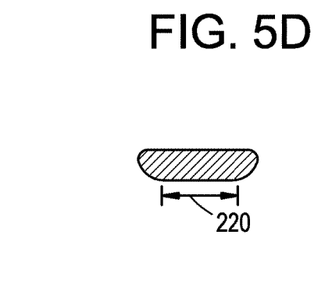
Figure 6A:
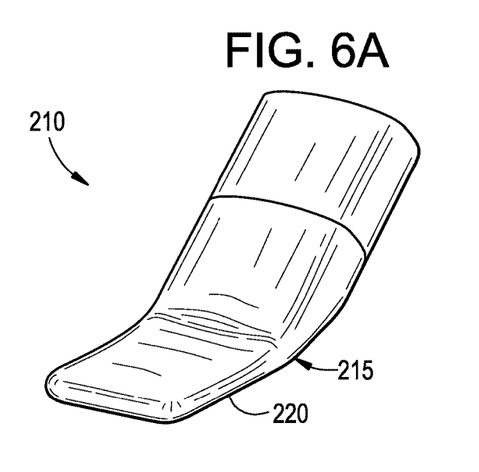
FIGS. 6A-6D depict perspective, top, side and cross-sectional views, respectively, of another embodiment of a tip of the applicator of FIG. 4.
Figure 6B:
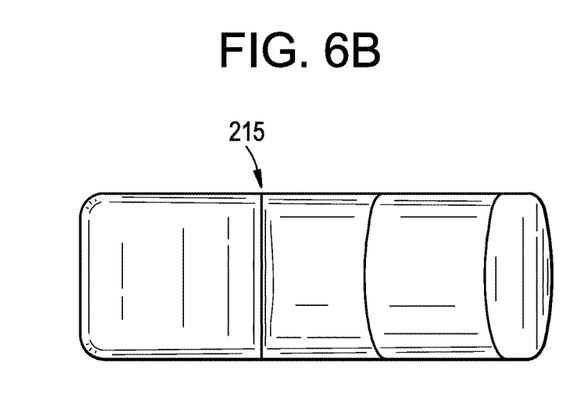
Figure 6C:
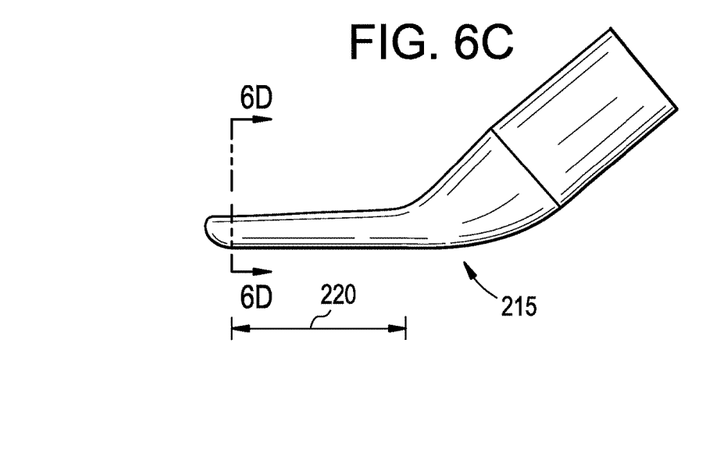
Figure 6D:
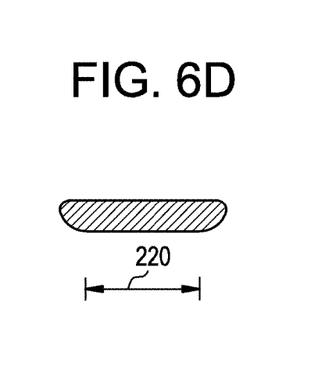

Upon extrusion of the material to a target tissue site, a user may desire to urge the material in one direction or another, for example such that the target tissue site is completely covered with the material. The user can manipulate the material following extrusion using the tip 115 of the applicator 100. Alternatively, a user may use another embodiment of an applicator 200 to manually deliver and/or manipulate the material. FIG. 4 depicts another embodiment of an applicator 200. The applicator 200 can include an elongate handle portion 205 and at least one tip 210. The tip 210 can be a generally short component coupled to one or both ends of the handle portion 205. As in previous embodiments, the tip 210 can be permanently or reversibly coupled to the handle portion 205.

As best shown in FIGS. 5A-5D and FIGS. 6A-6D, the tip 210 can include a bend 215 a distance away from where the tip 210 couples to the handle portion 205 and a contact surface 220. The bend 215 can be between about 20 degrees to about 45 degrees from the longitudinal axis of the tip 210. In an embodiment, the bend 215 is approximately 30 degrees from the longitudinal axis of the tip 210. The tip 210 can be formed of an elastomeric material and is configured to conform to a bone surface. The contact surface 220 of the tip 210 can also have one or more features that are fabricated from a material to which the composition can, to some degree, adhere. In some embodiments, the feature may include projecting or recessed surface texturing such as dimples, ridges, bristles, hairs. The feature can be rigid or flexible. The feature can allow for pre-loading of the tip 210 with an amount of the composition to be presented to the surgical site where the composition can then be applied, such as using a wiping motion.

In some embodiments, the tip (115, 210) is removably mounted to the barrel 110 or the handle 205. In other embodiments, the tip (115, 210) is mounted to a rigid member which can be attached to the barrel 110 or the handle 205.

A front end of the tip 210 can have a conic curvature. The curve moves away from horizontal plane more slowly than would a circular curve providing for an effectively larger contact surface 220 compared to a circular curved tip 210. The tip 210 can have a narrow contact surface 220 (see FIG. 5D) or a wider contact surface 220 (see FIG. 6D). The embodiment shown in FIG. 6D has an overall wider dimension that allows for more gentle curvature and larger contact surface 220. In an embodiment, the contact surface 220 is at least about 3 mm. In another embodiment, the contact surface 220 is at least about 4 mm. In another embodiment, the contact surface 220 is approximately 4 mm, 5 mm, 6 mm, 7 mm, 8 mm, 9 mm, 10 mm or greater in width. In another embodiment, the contact surface 220 is approximately 4 mm in width and the overall width of the tip is approximately 7 mm in width. In another embodiment, the contact surface 220 is approximately 7 mm in width and the overall width of the tip is approximately 10 mm in width. In an embodiment, the contact surface 220 is approximately 4 mm, 5 mm, 6 mm, 7 mm, 8 mm, 9 mm, 10 mm or greater in length.

As in previous embodiments, materials for the fabrication of the tip 210 can include, but are not limited to flexible medical polymers and rubbers, including thermoplastic elastomer (TPE) compounds such as VERSAFLEX CL e85, VERSAFLEX M 3060, MEDALIST MD320, PELLATHANE, and other similar TPEs. The tip 210 can also be formed of materials including, but not limited to, polyethylenes, polypropylene, acetals and other suitable resin candidates. The tip 210 can be formed of a generally elastomeric material. The material of the tip 210 can have a hardness of Shore A 30 to Shore A 110, Shore A 50 to Shore A 95, Shore A 75 to Shore A 85.

The applicator 100 can be manufactured pre-loaded with an amount of material housed in the barrel 110. The applicator 100 can be provided in a kit with or without a manual applicator 200. The kit can also be packaged with instructions for use and in a format convenient for surgical operating rooms, for example, in a box or in a sterile plastic wrapping or pouch, which can be sealed and sterilized. Different types of kits are contemplated herein and can be tailored to meet the needs of a particular method. In one embodiment, multiple removable tips of the applicator(s) are supplied in the kit (they may also be supplied individually in the absence of a kit). These tips may be of various widths (e.g. blade widths or tip diameters), lengths, angles, durometers, and/or shapes. Most often the removable tips will be mounted on a rigid material of the same nature as the handle or main body of the device. Thus in a syringe embodiment featuring a Pet-G barrel, the removable conical elastomeric tip with a bevel of approximately thirty degrees is mounted on an PET-G tube suitable for engagement with the distal portion of the PET-G syringe. Attachment of the tip to the delivery device may be by any means known to the art including, threaded attachments, bayonet attachments, snap on etc.

In some clinical embodiments, the biocompatible composition is pre-ejected such that a volume of the composition is exposed, and resides on a surface of the applicator tip. The composition can then be applied from the tip in a fashion similar to application with a spatula. Additional click(s) by a user can extrude more composition before, during or after wiping and application of the pre-extruded composition onto the surgical site.

In some clinical embodiments, the applicator or the spatula is used to wipe hemostatic putty—tamponade of Kronenthal (see Patent Application Serial Nos. 2006-0002976, filed Sep. 16, 2004; 2006-0280801, filed Jul. 25, 2006; and 2005-0065214, filed Sep. 16, 2004, the contents of which are incorporated herein by reference in their entireties) across the opening of a bleeding hole in bone, specifically a screw hole for securing of a surgical plate or pedicle screw. This mode of application allows for control of bleeding without filling of the entire hole, thereby employing a minimal amount of tamponade in the procedure. This method can allow effective tamponade such that bleeding from a hole several centimeters deep with as great as a 7.5 mm diameter can be staunched with as little as 0.15 cc, 0.2 cc, or 0.25 cc of composition. In some embodiments, the applicator or spatula can be used to spread hemostatic putty to the cut and bleeding edges of a medial sternotomy.

Figures 7A, 7B:
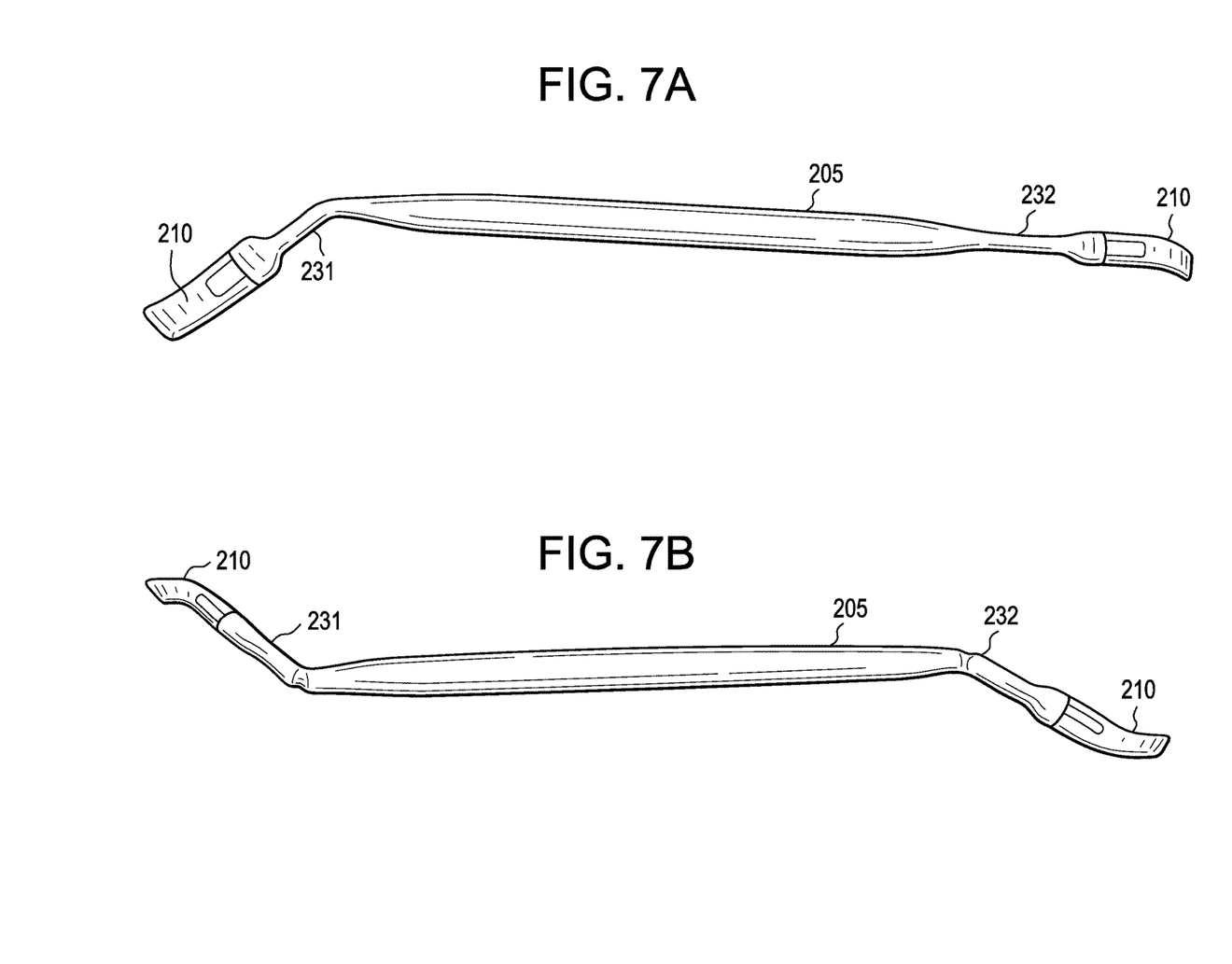
FIGS. 7A-7B depict top and bottom views, respectively, of yet another embodiment of an applicator.

The distal tips of the applicators may be oriented at any angle to the long axis of the handle. In some embodiments, the angle may vary from being parallel with to up to 90 degrees from the long axis of the handle. Relative to the angle of the delivery surface (i.e. tip bevel or blade angle) the angle may be varied according to need as well. For example, FIGS. 7A and 7B show an applicator having an elongated handle portion 205 connected to the tips via angled necks 231 and 232. The angles of the necks 231 and 232 may be preset during manufacturing. In some embodiments, one or both necks may be adjustable (e.g. includes an adjustable joint) or bendable (e.g. made of a flexible material) by hand to virtually any angle such that the angle may be adjusted (or bent) by the physician to change the delivery angle intraoperatively as desired for specific delivery needs. This is easily accomplished for the spatula embodiment through the use of a flexible polymer with shape memory. Eastar PET-G mn211 is an example of a suitable such polymer. For syringe or syringe-like applicators (e.g. applicator 100), the tips may be also oriented at an angle to the main axis of the device as desired.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An applicator for delivery of a viscous material to a surface of a surgical site, the applicator comprising:
   an elongate handle portion; and
   a tip coupled to a distal location of the handle portion and formed of an elastomeric material configured to conform to the surface of the surgical site, the tip comprising:
      an angular component providing a contact surface which is angled relative to a longitudinal axis of the tip;
      wherein the tip is mounted to a rigid member which is removably attached to the distal location of the handle portion; and
      wherein the contact surface comprises surface means for holding the viscous material and spreading the viscous material to the surface of the surgical site.

2. An applicator according to claim 1, wherein the surface of the surgical site is a bone surface.

3. An applicator according to claim 1, wherein the handle portion comprises a barrel connected to the tip for housing the viscous material, and a plunger for pumping the viscous material through the barrel to the tip.

4. An applicator according to claim 3, further comprising a metering means for metering an amount of the viscous material to be delivered to the surface of the surgical site.

5. An applicator according to claim 4, wherein the metering means comprises a series of grooves provided on the plunger and a click washer through which the plunger is inserted, wherein the grooves extend beneath an outer surface of the plunger.

6. An applicator according to claim 5, wherein the series of grooves are equally spaced.

7. An applicator according to claim 1, wherein the tip is coupled to the distal location of the handle portion via an angled neck.

8. An applicator according to claim 7, wherein the angled neck is adjustable.

9. An applicator according to claim 1, further comprising a heating element for heating the viscous material.

10. An applicator according to claim 1, wherein the surface means comprises one or more features consisting of a projecting surface, a recessed surface, surface texturing, dimples, ridges, bristles, and hairs.

11. An applicator according to claim 1, wherein the contact surface is angled at between 20 to 45 degrees from the longitudinal axis of the tip.

12. A kit comprising:
   a first applicator for delivering a viscous material to a surface of a surgical site, the first applicator comprising a barrel containing the viscous material within a central bore extending therethrough and a plunger for pumping the viscous material in the barrel; and
   one or more first tips connectable to an end of the barrel of the first applicator, the one or more first tips being made of an elastomeric material configured to conform to the surface of the surgical site and comprising a distal edge that is beveled across the diameter of the one or more first tips and forming a first contact surface which is angled relative to a longitudinal axis of the one or more first tips.

13. A kit according to claim 12, wherein the contact surface is angled at between 20 to 45 degrees from the longitudinal axis of the tip.

14. A kit according to claim 13, wherein the first applicator further comprises a metering means for metering an amount of the viscous material to be delivered to the surface of the surgical site.

15. A kit according to claim 13, wherein the metering means comprises a series of grooves provided on the plunger and a click washer through which the plunger is inserted wherein the grooves extend beneath an outer surface of the plunger.

16. A kit according to claim 15, wherein the series of grooves are equally spaced.

17. A kit according to claim 12, wherein the barrel further comprises an angled neck to which the one or more first tips can be connected.

18. A kit according to claim 17, wherein the angled neck is adjustable.

19. A kit according to claim 12, further comprising a heating element for heating the viscous material.

20. A kit according to claim 12, wherein the contact surface comprises a surface means for holding the viscous material that comprises one or more features consisting of a projecting surface, a recessed surface, surface texturing, dimples, ridges, bristles, and hairs.

21. A kit according to claim 12, further comprising:
one or more second tips formed from an elastomeric material configured to conform to the surface of the surgical site and comprising a second angular component providing a second contact surface which is angled relative to a longitudinal axis of the one or more second tips; and
a second applicator comprising an elongated handle portion having at least one end to which the one or more second tips can be connected.

22. A kit according to claim 21, wherein the second applicator further comprises an adjustable neck connected to the handle portion, the one or more tips being connectable to the adjustable neck.

23. A method for filing a hole in a bone surface, comprising:

mounting an applicator tip to a rigid member which is removably attached to a distal location of a handle portion of an applicator;
providing a viscous material on the applicator tip, the applicator tip being made of an elastomeric material configured to conform to a bone surface and comprising:
an angular component providing a contact surface located distal to a bend and one or more surface means for holding and spreading the viscous material; and
edges having a conic curvature; and
applying the viscous material intraoperatively to a hole in the bone surface using the contact surface of the applicator tip.

24. The applicator of claim 3, wherein outer surfaces of the tip and the barrel are flush with respect to one another at an interface between the tip and the barrel.

25. The applicator of claim 3, wherein the tip includes a lumen extending therethrough defining an inner surface and wherein the inner surface of the tip and an inner surface of the barrel are smooth at an interface between the tip and the barrel.

26. The applicator of claim 5, wherein the click washer comprises a central aperture dimensioned to receive the plunger and a series of teeth connected to an outer perimeter of the click washer and extending towards the central aperture, wherein the set of teeth are configured to reversibly interface with the grooves.

27. The applicator of claim 26, wherein the plurality of teeth comprise a first set of teeth alternating about the outer perimeter of the click washer with a second set of teeth, wherein a length of the second set of teeth is longer than a length of the first set of teeth.

28. The applicator of claim 3, wherein the tip further comprises a lumen extending therethrough and one edge of the tip extends outward to one side of the tip lumen to form a blade.

* * * * *